United States Patent
Toda

[19]

[11] Patent Number: 6,142,948
[45] Date of Patent: Nov. 7, 2000

[54] VIBRATION DISPLACEMENT DETECTING SYSTEM

[76] Inventor: Kohji Toda, 1-49-18 Futaba, Yokosuka 239-0814, Japan

[21] Appl. No.: 09/317,083

[22] Filed: May 21, 1999

[51] Int. Cl.$^7$ ....................................................... A61B 8/14
[52] U.S. Cl. ............................................. 600/459; 73/570
[58] Field of Search .................................. 600/437, 459, 600/462; 29/25.35; 73/625, 626, DIG. 1, 570; 310/313 B

[56] References Cited

U.S. PATENT DOCUMENTS

| | | | |
|---|---|---|---|
| 5,217,018 | 6/1993 | Dias ......................................... | 600/462 |
| 5,400,788 | 3/1995 | Dias et al. ............................... | 600/459 |
| 5,488,955 | 2/1996 | Dias ......................................... | 600/459 |

*Primary Examiner*—Marvin M. Lateef
*Assistant Examiner*—Ali M. Imam

[57] ABSTRACT

A vibration displacement detecting system comprises a piezoelectric substrate, input- and output interdigital transducers formed on an upper end surface of the piezoelectric substrate, a signal analyzing unit connected between the input- and output interdigital transducers, and a monitor. When an input electric signal is applied to the input interdigital transducer, a leaky elastic wave is excited in the piezoelectric substrate. The leaky elastic wave is radiated effectively in the form of a longitudinal wave into a matter being in contact with a lower end surface of the piezoelectric substrate. The longitudinal wave is reflected by a thing located inside the matter, and then, is detected at the output interdigital transducer as a delayed electric signal. If the thing vibrates mechanically, the delay time of the delayed electric signal changes. Thus, a vibration displacement generated by the thing is sensed in terms of a change in the delayed electric signal at the signal analyzing unit, and displayed on the monitor.

7 Claims, 8 Drawing Sheets

FIG.1

FIG.2 detecting assembly

VIBRATION DISPLACEMENT DETECTING SYSTEM

BACKGROUND OF THE INVENTION

1. Field of the Invention

The present invention related to a system for detecting a vibration displacement by means of using a detecting assembly composed of a piezoelectric substrate and input- and output interdigital transducers.

2. Description of the Prior Art

Conventional devices for detecting a vibration displacement are classified into two types. One is touch type, and the other is untouch type. Devices as an electric micrometer for measuring a minute displacement, a digital gauge for a small displacement, a rotary encoder for a rotation displacement, and a linear scale for a large displacement belong to the touch type. The rotary encoder is used for controlling a rotation velocity or a rotation frequency of a rotatory thing. The electric micrometer, the digital gauge or the linear scale is used as a reference for measuring the length of a thing, or used for inspection of machine. These touch type devices have some problems on measurement accuracy, response time, difficulty in use, durability and manufacturing. Devices as a laser-type sensor and an electroacoustic-type sensor belong to the untouch type. The laser-type sensor including a semiconductor position-sensing device is mainly used for measuring a vibration displacement along the direction vertical to the laser beam applied to a thing. The laser-type sensor has a defect that the longer the length of the laser beam, the lower the measurement accuracy because of flickering of the laser beam itself. In addition, the use of the laser-type sensor is impossible for the measurement in opaque media. The electroacoustic-type sensor is used for measuring the vibration displacement in a thing near a terminal of a pipe. The electroacoustic-type sensor has some problems on measurement accuracy, resistance for a change of circumstances, and so on.

SUMMARY OF THE INVENTION

An object of the present invention is to provide a vibration displacement detecting system capable of detecting a vibration displacement generated by a thing located inside a matter with a high sensitivity.

Another object of the present invention is to provide a vibration displacement detecting system capable of operating at a high frequency.

Another object of the present invention is to provide a vibration displacement detecting system capable of transducing a vibration displacement to an electric signal and displaying the vibration displacement on a monitor.

Another object of the present invention is to provide a vibration displacement detecting system excellent in measurement accuracy, response time, durability, and manufacturing.

A still other object of the present invention is to provide a vibration displacement detecting system easy in use and having a small size which is very light in weight and has a simple structure.

According to one aspect of the present invention there is provided a vibration displacement detecting system comprising a piezoelectric substrate, input- and output interdigital transducers formed on an upper end surface of the piezoelectric substrate, a signal analyzing unit connected between the input- and output interdigital transducers, and a monitor connected with the signal analyzing unit.

When an input electric signal is applied to the input interdigital transducer, a leaky elastic wave is excited in the piezoelectric substrate. The leaky elastic wave is radiated effectively in the form of a longitudinal wave into a matter in contact with a lower end surface of the piezoelectric substrate. A thing located inside the matter reflects the longitudinal wave. A reflected longitudinal wave is detected at the output interdigital transducer as a delayed electric signal. A vibration displacement generated by the thing can be sensed by the signal analyzing unit with a high sensitivity in terms of a change in the delayed electric signal, and then, displayed on the monitor.

According to another aspect of the present invention there is provided a liquid matter in contact with the lower end surface of the piezoelectric substrate.

According to another aspect of the present invention there is provided a cellular tissue and a blood vessel. The cellular tissue is in contact with the lower end surface of the piezoelectric substrate. The blood vessel is located inside the cellular tissue, and reflects the longitudinal wave.

According to another aspect of the present invention there is provided a piezoelectric substrate made of a piezoelectric ceramic, the polarization axis thereof being parallel to the thickness direction thereof.

According to another aspect of the present invention there is provided a piezoelectric substrate made of a piezoelectric polymer film.

According to other aspect of the present invention there is provided a signal analyzing unit comprising an amplifier and a frequency counter. The amplifier amplifies the delayed electric signal, and delivers an amplified electric signal. The input interdigital transducer receives a part of the amplified electric signal as the input electric signal. Thus, the input- and output interdigital transducers and the amplifier form a delay-line oscillator. On the other hand, the frequency counter counts a frequency of the amplified electric signal, and senses the vibration displacement in terms of a change in frequency of the amplified electric signal.

According to a further aspect of the present invention there is provided a signal analyzing unit comprising an amplifier and a frequency to voltage (F/V) converter. The amplifier amplifies the delayed electric signal, and delivers an amplified electric signal. The input interdigital transducer receives a part of the amplified electric signal as the input electric signal. Thus, the input- and output interdigital transducers and the amplifier form a delay-line oscillator. On the other hand, the F/V converter converts a frequency of the amplified electric signal into a voltage thereof, and senses the vibration displacement in terms of a change in voltage of the F/V converted electric signal.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
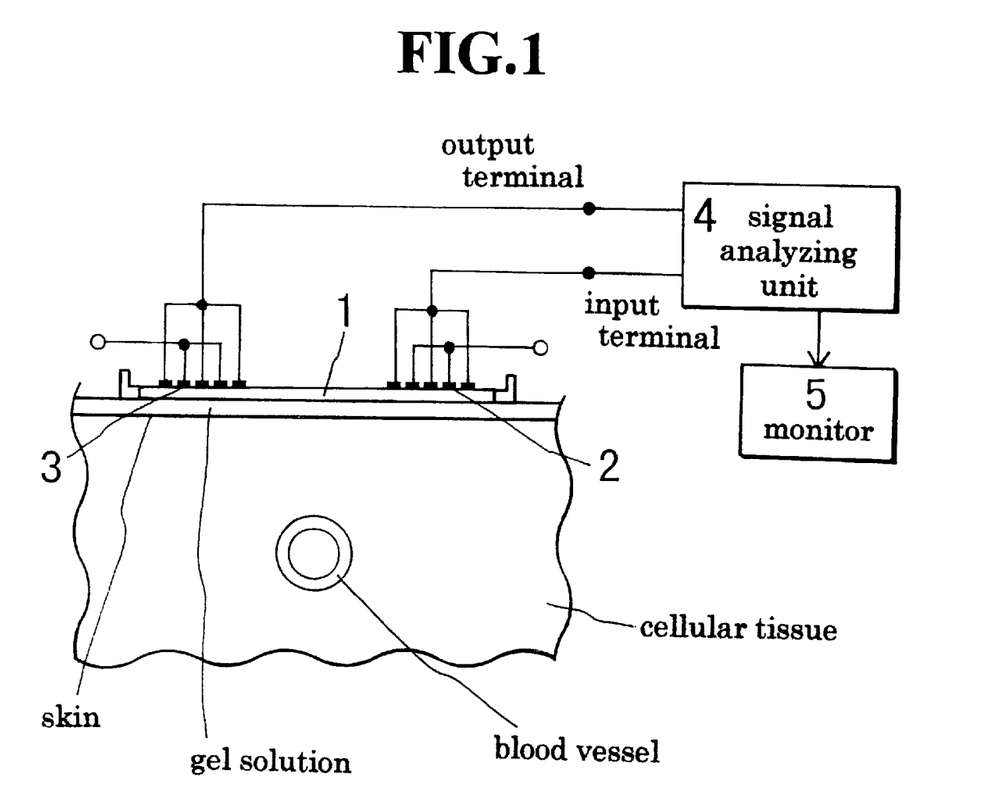
FIG. 1 shows a schematic illustration of a vibration displacement detecting system according to an embodiment of the present invention.

FIG. 1 shows a schematic illustration of a vibration displacement detecting system according to an embodiment of the present invention. The vibration displacement detecting system comprises piezoelectric substrate 1, input interdigital transducer 2 having an input terminal, output interdigital transducer 3 having an output terminal, signal analyzing unit 4, and monitor 5. Piezoelectric substrate 1 is made of a ceramic thin plate or a piezoelectric polymer film. Input interdigital transducer 2 and output interdigital transducer 3, having an arch-shape and made of an aluminum thin film, respectively, are formed on an upper end surface of piezoelectric substrate 1. Piezoelectric substrate 1, input interdigital transducer 2 and output interdigital transducer 3 form a detecting assembly. When sensing a vibration displacement generated by a thing located inside a matter, a lower end surface of piezoelectric substrate 1 is kept in contact with the matter. Thus, when sensing, for example, a person's pulse, that is a vibration displacement generated by a blood vessel in a cellular tissue, a lower end surface of piezoelectric substrate 1 is kept in contact with, for example, a human wrist. In addition, it is better to spread a gel solution on a skin near the blood vessel in the cellular tissue. Thus, the vibration displacement detecting system in FIG. 1 has a small size which is very light in weight and has a simple structure.

Figure 2:
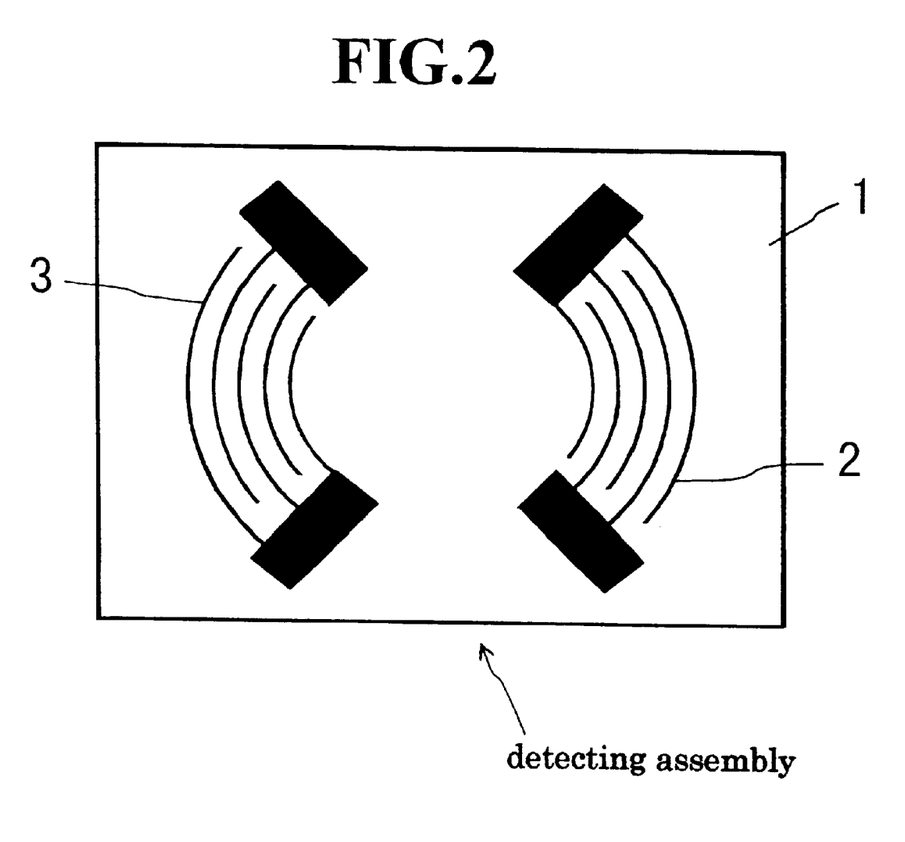
FIG. 2 shows a top plan view of the detecting assembly shown in FIG. 1.

FIG. 2 shows a top plan view of the detecting assembly shown in FIG. 1. The separation length between input interdigital transducer 2 and output interdigital transducer 3 is 6 mm. Input interdigital transducer 2 and output interdigital transducer 3 are arranged such that they make a pair with a concentric center, and have an aperture angle of 45°, an interdigital periodicity of 340 μm and 5 finger pairs, respectively. When sensing a person's pulse, the lower end surface of piezoelectric substrate 1 is put on the gel solution such that the concentric center of input interdigital transducer 2 and output interdigital transducer 3 is located just over the blood vessel.

Figure 3:
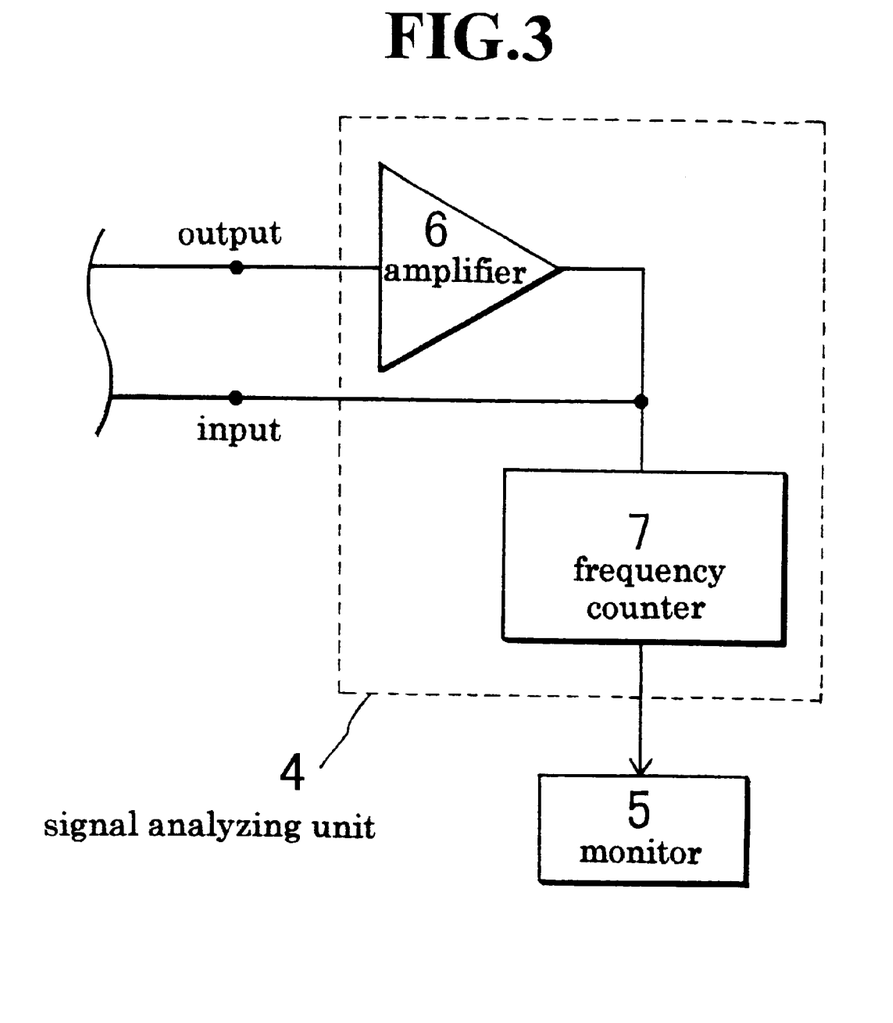
FIG. 3 shows a diagram of signal analyzing unit 4 according to a first embodiment.

FIG. 3 shows a diagram of signal analyzing unit 4 according to a first embodiment. Signal analyzing unit 4 comprises amplifier 6 and frequency counter 7.

In the vibration displacement detecting system in FIG. 1 with signal analyzing unit 4 in FIG. 3, if an input electric signal, with a frequency approximately corresponding to the interdigital periodicity of input interdigital transducer 2, is applied to input interdigital transducer 2, a leaky elastic wave is excited in piezoelectric substrate 1. Because piezoelectric substrate 1 is made of a piezoelectric ceramic, and in addition, the polarization axis thereof is parallel to the thickness direction thereof, the leaky elastic wave is excited in piezoelectric substrate 1 effectively. The leaky elastic wave having the wavelength approximately equivalent to the interdigital periodicity is radiated effectively in the form of a longitudinal wave into the cellular tissue through the gel solution, in other words, a mode conversion from the leaky elastic wave to the longitudinal wave in the cellular tissue occurs. Such effective radiation is owing to the arch-shape of input interdigital transducer 2, which enables an ultrasound beam to go along a slant direction to the lower end surface of piezoelectric substrate 1. The blood vessel reflects the longitudinal wave in the cellular tissue. A reflected longitudinal wave is detected at output interdigital transducer 3 as a delayed electric signal with a frequency approximately corresponding to the interdigital periodicity. Such detection of the delayed electric signal is due to the arch-shape of output interdigital transducer 3, which can detect an ultrasound beam from a slant direction to the lower end surface of piezoelectric substrate 1. The delayed electric signal is amplified via amplifier 6. A part of an amplified electric signal by amplifier 6 is applied to input interdigital transducer 2 again. Thus, input interdigital transducer 2, output interdigital transducer 3 and amplifier 6 form a self-oscillation type of delay-line oscillator. A remaining part of the amplified electric signal is transmitted to frequency counter 7. The frequency of the amplified electric signal is changed because of the continuous vibration of the blood vessel. Therefore, a vibration displacement by the blood vessel can be sensed by signal analyzing unit 4 with a high sensitivity in terms of a change in frequency of the amplified electric signal, and then, displayed on monitor 5.

Figure 4:
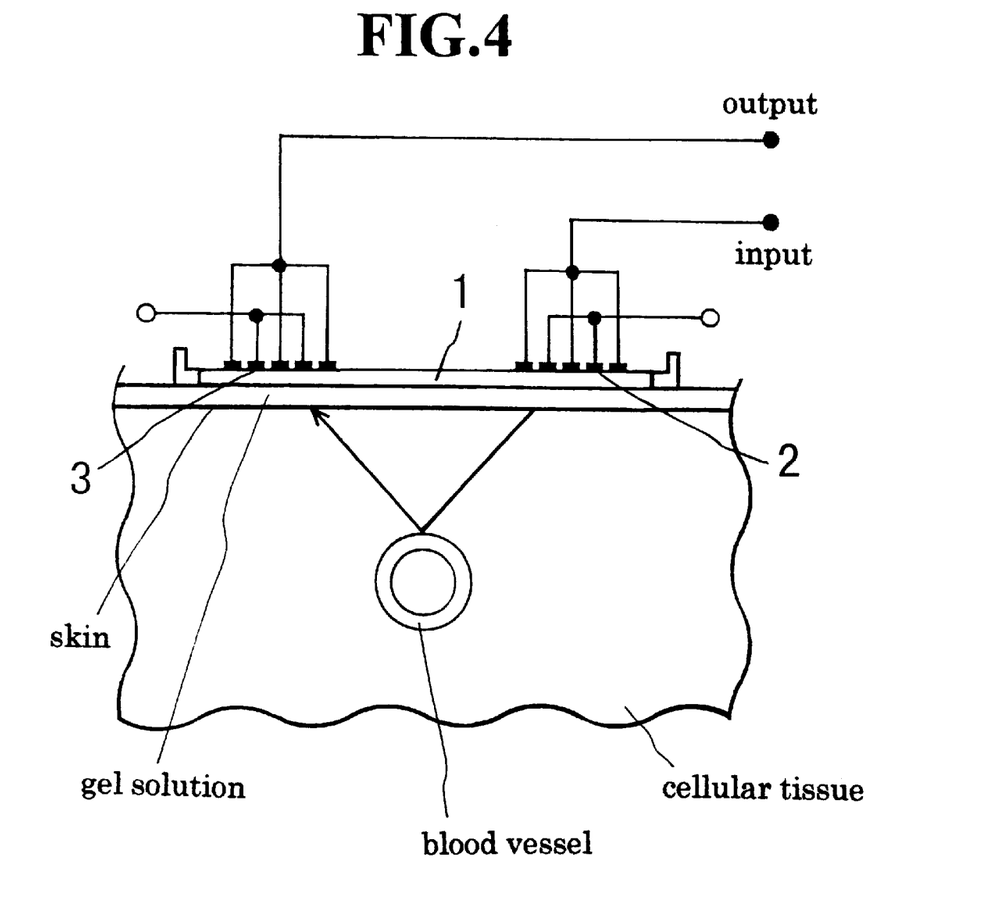
FIG. 4 shows an illustration exhibiting a path of the longitudinal wave traveling in the cellular tissue by an arrow.

FIG. 4 shows an illustration exhibiting a path of the longitudinal wave traveling in the cellular tissue by an arrow. Because the blood vessel vibrates continuously, a length of traveling path of the longitudinal wave is changed. A change in length of traveling path brings about a change in frequency of the amplified electric signal. Thus, a vibration displacement generated by the blood vessel can be sensed by signal analyzing unit 4 in terms of a change in frequency of the amplified electric signal, and then, is displayed on monitor 5.

Figure 5:
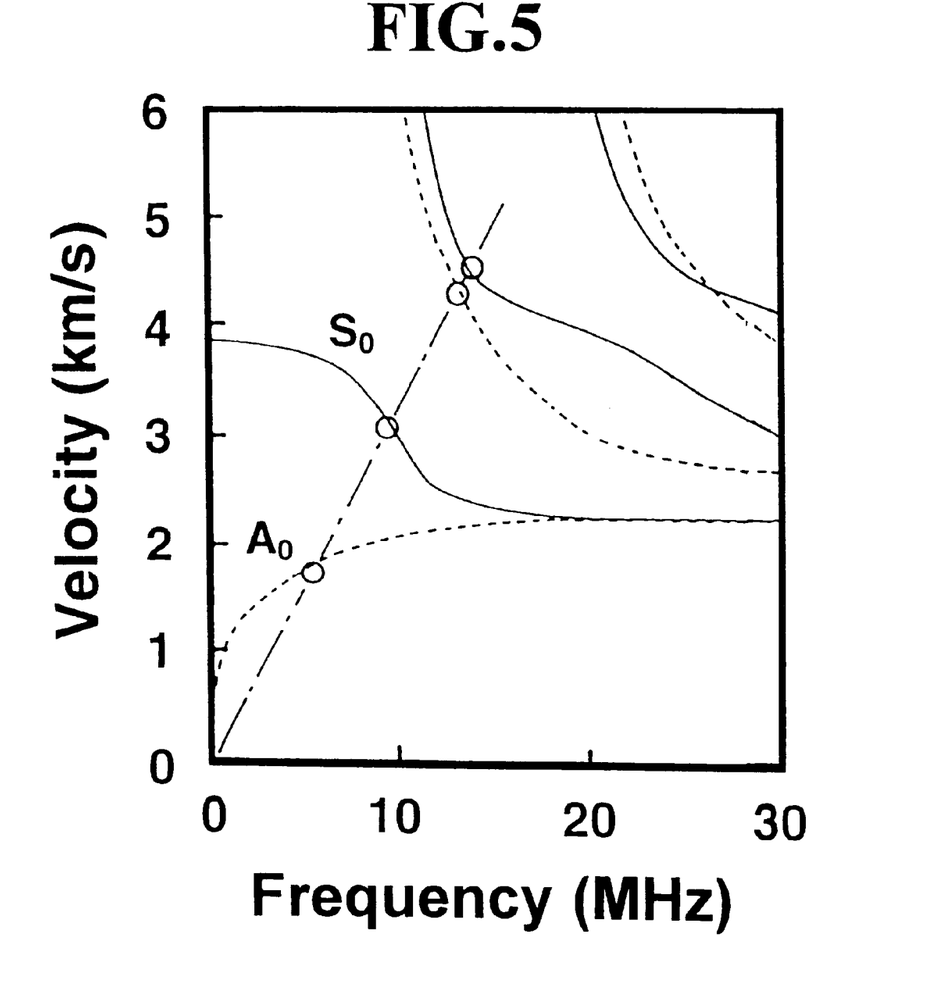
FIG. 5 shows a relationship between the frequency and the calculated phase velocity of a leaky elastic wave for each mode in piezoelectric substrate 1.

FIG. 5 shows a relationship between the frequency and the calculated phase velocity of a leaky elastic wave for each mode in piezoelectric substrate 1.

Piezoelectric substrate 1 has a shear wave velocity of 2,450 m/s and a longitudinal wave velocity of 4,390 m/s. A large velocity-dispersion for each mode is recognized.

Figure 6:
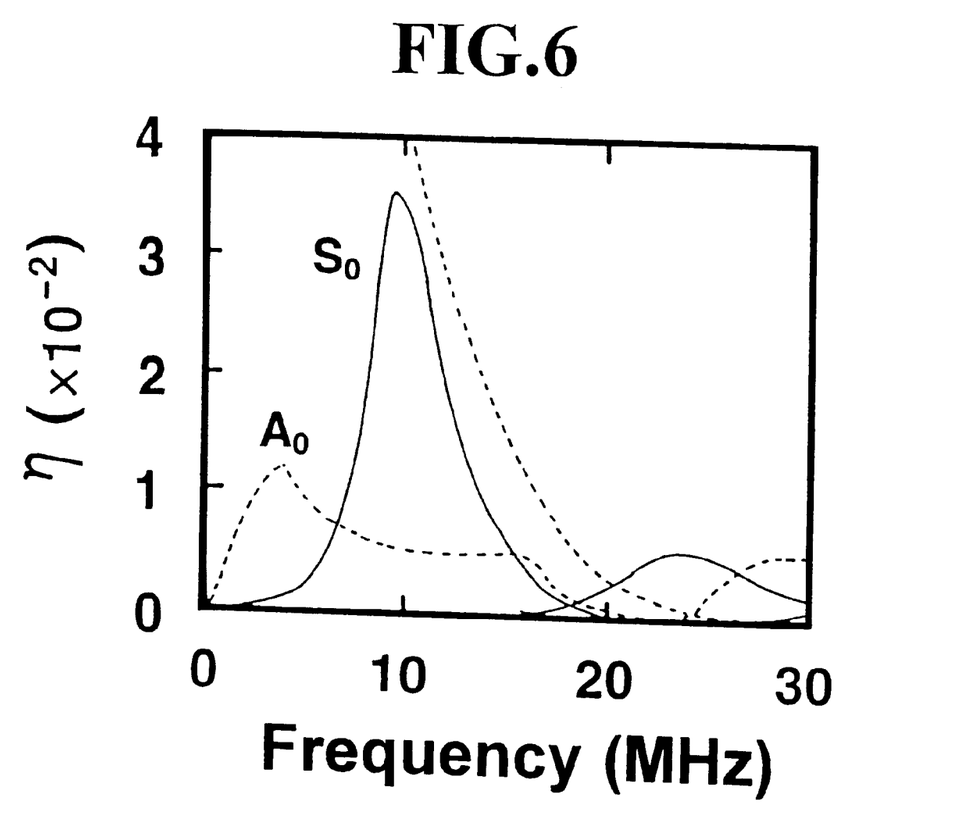
FIG. 6 shows a relationship between the frequency and the calculated transducer efficiency η for a longitudinal wave radiation into a liquid.

FIG. 6 shows a relationship between the frequency and the calculated transducer efficiency η for a longitudinal wave radiation into a liquid (water). It should be noted that the $S_0$ mode curve has the highest peak at around 9.5 MHz, that is the most appropriate operation frequency.

It is possible to sense a vibration displacement caused by pouring water into a tube located in a liquid. In this case, the liquid corresponds to a liquid layer composed of the gel solution and the cellular tissue, and the tube corresponds to the blood vessel, in FIG. 1. When water is poured into the tube, a dimension of the tube in diameter is changed, causing variation in length of traveling path of the longitudinal wave in the liquid. Such a variation in length of traveling path is detected in terms of a change in frequency of the amplified electric signal.

Figure 7:
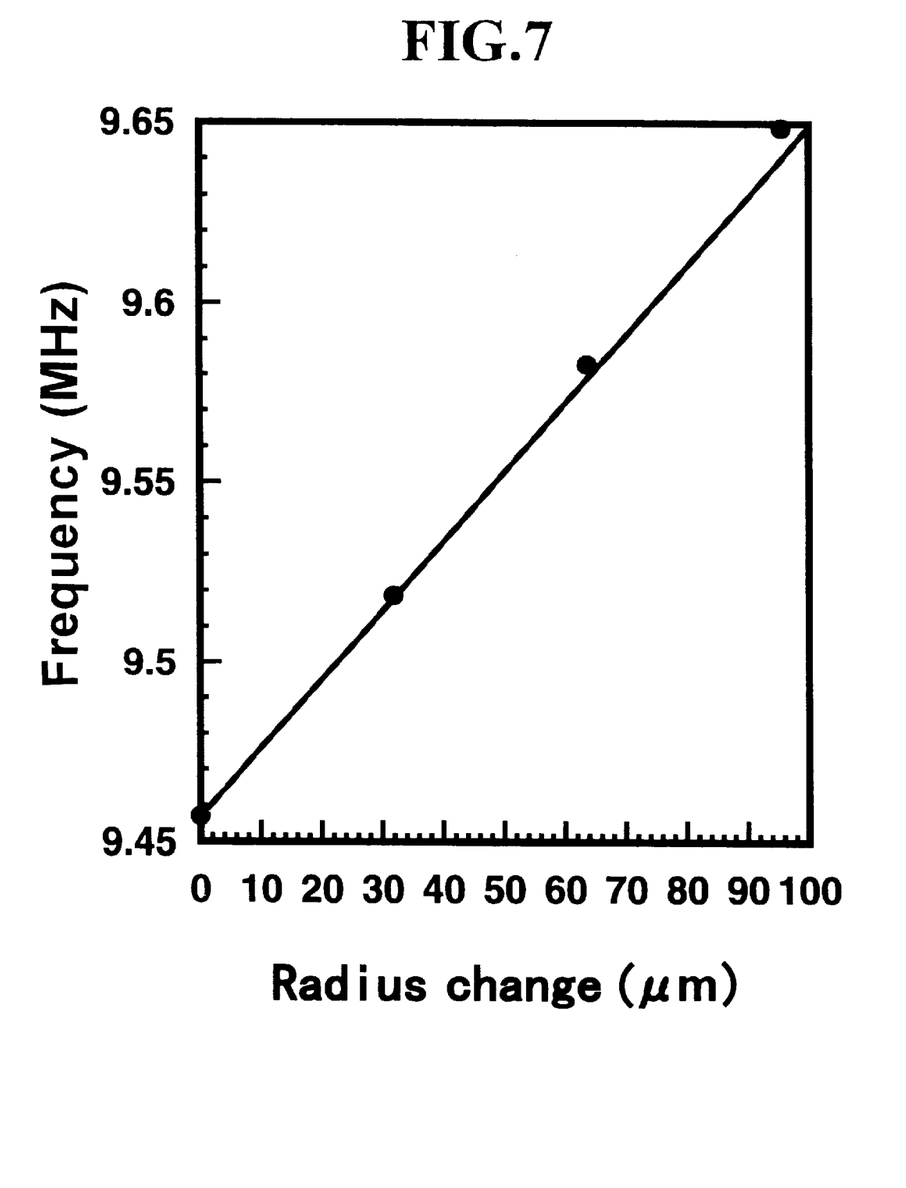
FIG. 7 shows a relationship between the frequency of the amplified electric signal, and the radius change of the tube when water is poured into the tube.

FIG. 7 shows a relationship between the frequency of the amplified electric signal, and the radius change of the tube when water is poured into the tube located in the liquid. In this case, water is poured via one terminal of the tube, the other terminal of the tube being closed. It is clear that the frequency is linearly correlated to the radius change of the tube. Thus, it is possible to sense a displacement generated by pouring water into the tube in terms of a change in frequency.

Figure 8:
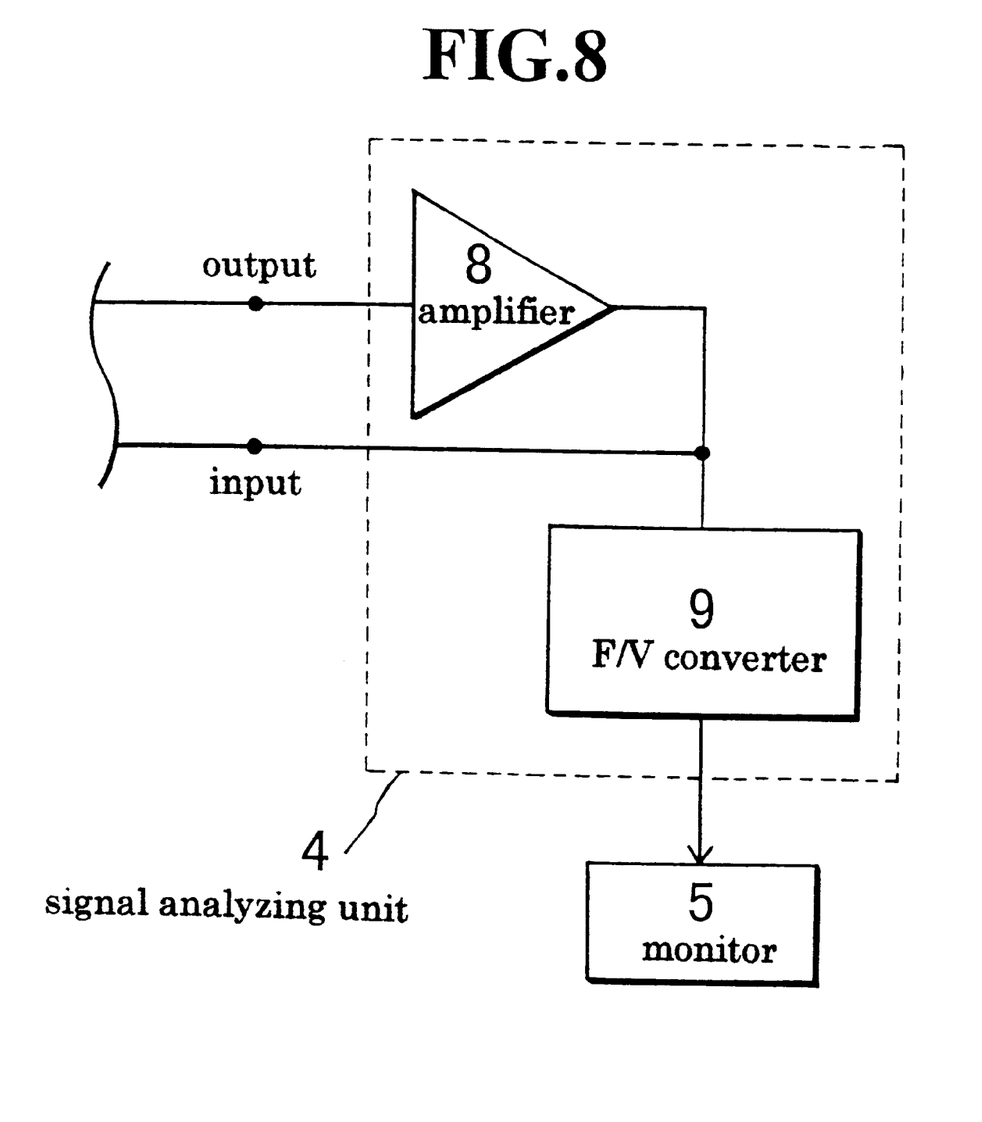
FIG. 8 shows a diagram of signal analyzing unit 4 according to a second embodiment.

FIG. 8 shows a diagram of signal analyzing unit 4 according to a second embodiment. Signal analyzing unit 4 comprises amplifier 8, and frequency to voltage (F/V) converter 9.

In the vibration displacement detecting system in FIG. 1 with signal analyzing unit 4 in FIG. 8, if an input electric signal is applied to input interdigital transducer 2, a leaky elastic wave is excited in piezoelectric substrate 1. The leaky elastic wave is radiated effectively in the form of a longitudinal wave into the cellular tissue through the gel solution. The longitudinal wave reflected at the blood vessel is detected at output interdigital transducer 3 as a delayed electric signal. The delayed electric signal is amplified via amplifier 8. A part of an amplified electric signal by amplifier 8 is applied to input interdigital transducer 2 again. Thus, input interdigital transducer 2, output interdigital transducer 3 and amplifier 8 form a self-oscillation type of delay-line oscillator. A remaining part of the amplified electric signal is transmitted to F/V converter 9. If the continuous vibration in the blood vessel is sensed by signal analyzing unit 4, a voltage is obtained in the form corresponding to the vibration. Therefore, a vibration displacement by the blood vessel can be sensed in terms of a change in voltage of the F/V converted electric signal, and then, displayed on monitor 5.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A vibration displacement detecting system comprising:

a piezoelectric substrate having an upper- and a lower end surfaces being parallel to each other, said lower end surface being in contact with a matter;

an input interdigital transducer having an arch-shape and formed on said upper end surface of said piezoelectric substrate, the thickness of said piezoelectric substrate being smaller than an interdigital periodicity of said input interdigital transducer;

an output interdigital transducer having an arch-shape and formed on said upper end surface of said piezoelectric substrate, said input- and output interdigital transducers making a pair with a concentric center;

a signal analyzing unit connected between said input- and output interdigital transducers; and a monitor connected with said signal analyzing unit, said piezoelectric substrate, and said input- and output interdigital transducers forming a detecting assembly, said input interdigital transducer receiving an input electric signal with a frequency approximately corresponding to said interdigital periodicity, exciting a leaky elastic wave in said piezoelectric substrate, causing a mode conversion from said leaky elastic wave, having the wavelength approximately equivalent to said interdigital periodicity, to a longitudinal wave in said matter, making a thing located inside said matter reflect said longitudinal wave back, said output interdigital transducer detecting a reflected longitudinal wave as a delayed electric signal with a frequency approximately corresponding to said interdigital periodicity, said signal analyzing unit sensing a vibration displacement generated by said thing in terms of a change in said delayed electric signal, and said monitor displaying said vibration displacement.

2. A vibration displacement detecting system as defined in claim 1, wherein said matter is a liquid matter.

3. A vibration displacement detecting system as defined in claim 1, wherein said matter is a cellular tissue, and said thing is a blood vessel.

4. A vibration displacement detecting system as defined in claim 1, wherein said piezoelectric substrate is made of a piezoelectric ceramic, the polarization axis thereof being parallel to the thickness direction thereof.

5. A vibration displacement detecting system as defined in claim 1, wherein said piezoelectric substrate is made of a piezoelectric polymer film.

6. A vibration displacement detecting system as defined in claim 1, wherein said signal analyzing unit comprising:

an amplifier amplifying said delayed electric signal and delivering an amplified electric signal, said input interdigital transducer receiving a part of said amplified electric signal as said input electric signal, said input- and output interdigital transducers and said amplifier forming a delay-line oscillator, and a frequency counter counting a frequency of said amplified electric signal, and sensing said vibration displacement in terms of a change in frequency of said amplified electric signal.

7. A vibration displacement detecting system as defined in claim 1, wherein said signal analyzing unit comprising:

an amplifier amplifying said delayed electric signal and delivering an amplified electric signal, said input interdigital transducer receiving a part of said amplified electric signal as said input electric signal, said input- and output interdigital transducers and said amplifier forming a delay-line oscillator, and a frequency to voltage converter converting a frequency of said amplified electric signal into a voltage thereof, and sensing said vibration displacement in terms of a change in voltage of the converted electric signal by said converter.

* * * * *